United States Patent
Salini

[11] Patent Number: 5,637,304
[45] Date of Patent: Jun. 10, 1997

[54] COSMETICAL OR PHARMACEUTICAL COMPOSITIONS COMPRISING DEACYLATED GLYCEROPHOSPHOLIPIDS FOR TOPICAL USE

[75] Inventor: Alberto Salini, Stabio, Switzerland

[73] Assignee: Flarer S.A. Pharmaceutical Fine Chemicals, Stabio, Switzerland

[21] Appl. No.: 313,210

[22] PCT Filed: Mar. 26, 1993

[86] PCT No.: PCT/EP93/00746

§ 371 Date: Sep. 28, 1994

§ 102(e) Date: Sep. 28, 1994

[87] PCT Pub. No.: WO93/19730

PCT Pub. Date: Oct. 14, 1993

[30] Foreign Application Priority Data

Mar. 30, 1992 [CH] Switzerland ............ 01004/92

[51] Int. Cl.$^6$ ............ A61K 7/00; A61K 7/025; A61K 7/032; A61K 7/06
[52] U.S. Cl. ............ 424/401; 424/63; 424/64; 424/70.1; 424/70.7; 514/844; 514/845; 514/846; 514/847; 514/880; 514/881; 514/944

[58] Field of Search ............ 424/401, 70.1, 424/70.7, 63, 64; 514/78, 844–847, 944, 880, 881

[56] References Cited

U.S. PATENT DOCUMENTS

| | | | |
|---|---|---|---|
| 4,424,234 | 1/1984 | Alderson | 424/317 |
| 5,089,269 | 2/1992 | Noda | 424/456 |
| 5,208,031 | 5/1993 | Kelly | 424/412 |
| 5,315,023 | 5/1994 | De Ferra | 558/146 |

FOREIGN PATENT DOCUMENTS

| | | |
|---|---|---|
| 0255937 | 2/1988 | European Pat. Off. . |
| 0407995 | 1/1991 | European Pat. Off. . |
| 1016890 | 1/1989 | Japan . |
| 2101086 | 4/1990 | Japan . |

*Primary Examiner*—Gollamudi S. Kishore
*Attorney, Agent, or Firm*—Bucknam and Archer

[57] ABSTRACT

Deacylated glycerophospholipids, such as L-α-glycerylphosphorylcholine, L-α-glycerylphosphorylethanolamine, L-α-glycerylphosphorylserine, L-α-glycerylphosphoryl-D-myo-inositol are effective for topical use and may be incorporated into cosmetic or pharmaceutical compositions.

12 Claims, No Drawings

COSMETICAL OR PHARMACEUTICAL COMPOSITIONS COMPRISING DEACYLATED GLYCEROPHOSPHOLIPIDS FOR TOPICAL USE

FIELD OF THE INVENTION

The invention relates to the topical use of deacylated glycerophospholipids and of the physiologically acceptable salts thereof.

Particularly, the invention relates to the use of deacylated glycerophospholipids named L-α-glycerylphosphorylcholine, L-α-glycerylphosphorylethanolamine, L-α-cglycerylphosphorylserine, L-α-cglycerylphosphoryl-D-myo-inositol, respectively.

These compounds, in the present invention, can be used alone or in mixtures thereof.

BACKGROUND OF THE INVENTION

The deacylated glycerophospholipids are mainly obtained by the semisynthetic route, for example those preferred in the present invention are obtained by selective deacylation of the natural phospholipids extracted from soy.

Glycerophospholipids are compounds widely occurring in nature, where they exert important biological functions, for example they are the main lipid components of cell phospholipids.

Their administration by the oral and parenteral routes, for example as diet supplements or as medicaments, proved to be useful in the prevention of the involution processes of the cell membranes, since they can play an important role on the biochemical lesions occurring on the membrane phospholipids.

SUMMARY OF THE INVENTION

Now it has surprisingly been found that the deacylated glycerophospholipids of the present invention can be adsorbed by the topical route, if suitably formulated, and this is a valuable alternative to the exogenous supply to the skin cells.

Deacylated glycerophospholipids, mainly those preferred in the present invention, have interesting properties which can suitably be exploited also in the cosmetic field.

The use of the glycerophospholipids is based on the fact that these compounds can be considered both as basic substances (for the formulation of excipients) and as specializing functional substances.

As basic substances, they can be used, for example, to give wetting, antidehydrating, plasticizing, co-solvent and co preservative properties.

As specializing functional substances, they can be used, for instance, as moisturizers, emollients, elasticizers, restitutives and the like.

These compounds can usefully be applied also to the hair cosmetic, for example as antistatics, restitutives, voluminizing agents and the like.

The used concentrations of the deacylated glycerophospholipids in the present invention can vary within wide ranges, according to the envisaged uses and the kind of the prepared formulation; for example they can be used in a range from 0.01% up to 50% by weight, preferably from 0.1% to 10%.

The deacylated phospholipids have a very low systemic toxicity as well as a particularly low topical toxicity, as evidenced by the tests carried out in the animal, hereinafter described.

Cutaneous sensitization

350–450 g guinea pigs, depilated on the back, were used.

50 mg of the product were applied on the left side of the depilated area every other day for 15 days. 30–35 days from the beginning of the treatment, 50 mg of the product were applied on the right side of the back, and the observations were recorded during 24 hours.

No cutaneous reactions were observed during the treatment and in the final phase of antigenic induction.

Eye Irritation

The eye tolerance was determined on New Zealand rabbits.

0.1 ml of a 1% solution of the product were instilled into the conjunctival sac of the right eye of the rabbit, whereas 0.1 ml of saline solution were instilled into the left eye.

The eyes were carefully checked for a time of 24 hours, recording any anomalies.

Immediately after the administration of the product and of the saline solution, an abundant lachrymation was observed. Subsequently conjunctiva, iris and cornea remained normal during the whole observation time.

Cutaneous Irritation

350–450 g guinea pigs were used, which were depilated on the back by means of a razor.

4 Product doses, corresponding to 50 mg–100 mg–200 mg–300 mg, were applied, then observation started, which lasted 24 hours at least.

No cutaneous irritations were observed at the various product doses.

The formulations containing the deacylated phospholipids of the present invention are those known in the art of the dermatological and cosmetic formulations, preferably those containing water as the excipient.

The moisturizing action of L-α-glycerylphosphorylcholine was evidenced carrying out the test described hereinbelow.

Moisturizing Activity

18 Albino Sprague-Dawley male rats, weighing 150 g (+/−20), were used, which were depilated on the back by means of a commercially available depilatory cream, randomly subdivided into 3 groups of 6 animals each and treated for 14 consecutive days, once in the morning and once at night, with:

$1^{st}$ group: 0.2 g/day of white vaseline $2^{nd}$ group: 0.2 g/day of 0.1% glycerylphosphorylcholine in white vaseline.

When treatment was over, the animals were killed by prolonged ether anaesthesia, cutis was removed from the treated area and carefully laid on a cork board, then 3 small cutis cylinders were taken from the same anatomic area by means of a cork-piercer, dried for 48 hours at 60° C. in a dry oven, then weighed again.

The cutis hydration conditions were obtained by the difference between the cutis cylinder weight before and after drying.

The glycerylphosphorylcholine treatment, extended for 2 weeks at a frequency of two daily treatments, could increase the amount of water contained in the cutis of the treated animals, in a statistically significant way compared with white vaseline-treated controls (Table 1).

TABLE 1

| Rat n. | sample n. | Water content (mg) in the cutis | |
|---|---|---|---|
| | | controls | glycerylphosphorylcholine |
| 1 | 1 | 230 | 255 |
| | 2 | 238 | 247 |
| | 3 | 261 | 277 |
| 2 | 1 | 220 | 249 |
| | 2 | 238 | 250 |
| | 3 | 248 | 266 |
| 3 | 1 | 270 | 259 |
| | 2 | 263 | 268 |
| | 3 | 256 | 265 |
| 4 | 1 | 233 | 245 |
| | 2 | 248 | 262 |
| | 3 | 230 | 255 |
| 5 | 1 | 210 | 274 |
| | 2 | 220 | 281 |
| | 3 | 230 | 257 |
| 6 | 1 | 240 | 283 |
| | 2 | 235 | 270 |
| | 3 | 255 | 295 |
| Mean | | 240.27 | 264.33 |
| +/− S.E. | | 3.86 | 3.25 |
| P | | — | <0.01 |

The following example further illustrate the invention.

EXAMPLES

| MASCARA GEL | |
|---|---|
| A) 1,2-Propanediol | 2.0% |
| Preservants | q.s. |
| Glycerylphosphorylcholine 85° in water | 0.2% |
| Pearl lustre pigment (E. Merck Darmstadt) | 0.004% |
| Carbomer 940 | 0.2% |
| B) Triethanolamine | 0.2% |
| Demineralized water | 18.2% |
| C) 95° Ethanol | 10.0% |
| Polyvinylpyrrolidone (K 30) | 1.0% |

Preparation:

1,2-Propanediol glycerylphosphorylcholine and water were mixed together, then Pearl lustre pigment and subsequently Carbomer 940 were added, stirring strongly. The mixture was neutralized with aqueous triethanolarain Ethanol and polyvinylpyrrolidone (K 30) were added under stirring.

| EYE POWDER | |
|---|---|
| Pigment | 30.0% |
| Glycerylphosphoryl-inositol calcium salt | 0.5% |
| Talc | 49.0% |
| Potato starch | 7.5% |
| Magnesium stearate | 2.5% |
| Binder | 10.5% |
| (composition of the binder: | |
| cetyl palmitate | 5% |
| petroleum | 9% |
| perfume | q.s. |
| preservants | q.s. |
| isopropyl stearate q.s. to | 100.0%) |

Preparation:

The powder ingredients were mixed thoroughly. The binder, in the molten state, was added in portions under stirring.

Finally the mixture was compressed under 40–60 bars (560–840 psi).

| NUTRITIVE CREAM | |
|---|---|
| A) Glycerylphosphorylcholine | 2.0% |
| Glycerin | 2.0% |
| Copper pyroglutamate | 0.2% |
| Zinc pyroglutamate | 0.2 |
| B) Glycerol monostearate emulsified with | |
| Polyethylene glycol | 5.0% |
| Stearic acid | 8.0% |
| Myristyl ethoxy myristate | 6.0% |
| Sweet almond oil | 9.0% |
| Cetyl alcohol | 1.0% |
| Lauryl pyroglutamate | 1.0% |
| Silicon | 0.5% |
| Triethanolamine | q.s. |
| Perfume | q.s. |
| Demineralized water q.s. to | 100.0% |

Preparation

Mix the components of phase A) and water and heat to 70°.

Mix the components of phase B) and heat to 70°. Add phase A) to phase B) slowly stirring. Add triethanolamine to the mixture to pH 6.4, then add the perfume and dilute to 100 with water. Cool to 35° stirring slowly.

| SHAMPOO | |
|---|---|
| 28% Sodium lauryl ether sulfate | 40.0% |
| Coconut fatty acid diethanolamide | 4.0% |
| 85% Glycerylphosphorylcholine in water | 1.0% |
| Sodium chloride | 4.0% |
| Perfumes and preservants | q.s. |
| Deionized water q.s. to | 100.0% |

Preparation:

The components are mixed with water in the described order, stirring slowly.

| HAIR GEL (WET GEL) | |
|---|---|
| Carbomer 940 | 1.0% |
| Triethanolamine (TEA) | 1.3% |
| Glycerylphosphorylserine | 0.7% |
| Pearl lustre pigment (E. Merck, Darmstad) | 0.2% |
| Perfume and preservants | q.s. |
| Deionized water q.s. to | 100.0% |

Preparation:

The pigment is dispersed in the water-alcohol mixture, stirring strongly.

Carbomer 940 is added and after complete dissolution, TEA is added to neutralize.

Finally the remaining components are added continuing stirring until homogeneous dispersion.

| MAKE-UP CREAM | |
|---|---|
| A) Silicons | 10% |
| (Cycometicon and Dimeticon Copolyol) | |
| Silicon (Cycometicon) | 10% |
| Bee wax | |
| Polyglyceryl-4-oleate | 2% |
| Glycerylphosphorylethanolamine | 1% |

MAKE-UP CREAM

|  |  |
|---|---|
| Pigments | 18% |
| B) Sodium citrate | 3% |
| Preservants | q.s. |
| Water q.s. to | 100% |

Preparation:

Silicons, bee wax and polyglyceryl-4-oleate are mixed together and heated to 70°; the remaining components of the phase A) are added, dissolving them in water. Phase A) is added to phase B) allowing the mixture to cool.

Finally the cream is homogenized.

LIP GLOSS

|  |  |
|---|---|
| Castor-oil | 70.0% |
| Miglyol ® 812 (caprylic/capric triglycerid) | 20.0% |
| Bee wax | 2.5% |
| Carnauba wax | 2.2% |
| Glycerylphosphoryl serine calcium salt | 0.3% |
| Pigment | 5.0% |
| Flavours and preservants q.s. to | 100.0% |

Preparation:

The mixed oils and waxes are heated to melting.

The molten mass is stirred and the deacylated glycerophospholipide, pigment and perfume are added.

The mixture is placed into containers at 50°–60° C.

RESTITUTIVE HYDRATING GEL

|  |  |
|---|---|
| Carbomer 940 | 10.0% |
| Triethanolamine | 12.5% |
| Glycerylphosphorylcholine | 0.1% |
| Glycerylphosphorylserine | 0.1% |
| Glycerylphosphorylethanolamine | 0.1% |
| Glycerylphosphorylinositol | 0.1% |
| Preservant and perfume | q.s. |
| Deionized water q.s. to | 100.0% |

Preparation:

Carbomer 940 is dispersed in water and neutralized with triethanolamine; then the remaining components are added in the indicated order, stirring slowly.

DERMATOLOGICAL HYDRATING LOTION

|  |  |
|---|---|
| Glycerylphosphorylcholine | 40.0% |
| Propyl p-oxybenzoate (preservant) | 0.3% |
| Methyl p-oxybenzoate | 0.7% |
| Deionized water q.s. to | 100.0% |

Preparation:

The preservants are warm dissolved in deionized water, then the deacylated glycerophospholipide is added.

Use: apply more times a day on chapped, reddened, dry skin and the like.

I claim:

1. A pharmaceutical and cosmetic composition for topical application containing 0.01–50% by weight of a deacylated glycerophospholipid which is a member selected from the group consisting of L-α-glycerylphosphorylcholine, L-α-glycerylphosphorylethanolamine, L-α-glycerylphosphorylserine, L-α-glycerylphosphoryl-D-myo-inositol, salts thereof, mixtures thereof and excipients, said composition is in the form of a mascara gel, eye powder, nutritive cream, shampoo, hair gel, make-up cream, lip gloss, restitutive hydrating gel or a dermatological hydrating lotion.

2. The composition according to claim 1 wherein water is an excipient.

3. A mascara gel according to claim 1 which contains L-α-glycerylphosphorylcholine, water, ethanol, polyvinylpyrrolidone and 1,2-propanediol.

4. An eye powder according to claim 1 which contains L-α-glycerylphosphoryl inositol calcium salt, a pigment, talc, potato starch, magnesium stearate and a binder.

5. A nutritive cream according to claim 1 which contains L-α-glycerylphosphorylcholine, glycerine, polyethylene glycol, myristyl ethoxy myristate, sweet almond oil and water.

6. A shampoo according to claim 1 which contains L-α-glycerylphosphorylcholine, sodium lauryl ether sulfate, coconut fatty acid diethanolamide, sodium chloride and water.

7. A hair gel according to claim 1 which contains L-α-glycerylphosphorylserine, triethanolamine, a pigment and water.

8. A make-up cream according to claim 1 which contains L-α-glycerylphosphorylethanolamine, a silicone, polyglyceryl 4-oleate, pigments, sodium citrate and water.

9. A lip gloss according to claim 1 which contains L-α-glycerylphosphorylserine calcium salt, castor oil, bee wax, carnauba wax and a pigment.

10. A restitutive hydrating gel according to claim 1 which contains L-α-glycerylphosphorylcholine, L-α-glycerylphorylethanolamine, L-α-glycerylphosphorylserine, L-α-glycerylphosphorylinositol, L-α-triethanolamine and water.

11. A dermatological hydrating lotion according to claim 1 which contains L-α-glycerylphosphorylcholine, propyl p-oxybenzoate, methyl p-oxybenzoate and water.

12. A method of treatment of a living subject in need of a cosmetic, restitutive cream, nutritive cream, which consists of applying topically to said living subject, a composition containing 0.01–50% by weight of a deacylated glycerophospholipid which is a member selected from the group consisting of L-α-glycerylphosphorylcholine, L-α-glycerylphosphorylethanolamine, L-α-glycerylphosphorylserine, L-α-glycerylphosphoryl-D myo-inositol, salt thereof, mixtures thereof and excipients, said composition is in the form of a cosmetic, restitutive cream or a nutritive cream.

* * * * *